United States Patent
Pulliam et al.

(10) Patent No.: US 9,744,017 B2
(45) Date of Patent: Aug. 29, 2017

(54) VAGINAL VAULT SUSPENSION DEVICE AND METHOD

(71) Applicant: The General Hospital Corporation, Boston, MA (US)

(72) Inventors: Samantha J. Pulliam, Beverly, MA (US); Milena M. Weinstein, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/146,240

(22) Filed: May 4, 2016

(65) Prior Publication Data

US 2016/0242888 A1   Aug. 25, 2016

Related U.S. Application Data

(63) Continuation of application No. 13/497,181, filed as application No. PCT/US2010/049308 on Sep. 17, 2010, now Pat. No. 9,333,064.

(60) Provisional application No. 61/245,149, filed on Sep. 23, 2009.

(51) Int. Cl.
| | |
|---|---|
| *A61F 2/04* | (2013.01) |
| *A61F 2/00* | (2006.01) |
| *A61B 17/062* | (2006.01) |
| *A61L 31/16* | (2006.01) |
| *A61B 17/42* | (2006.01) |
| *A61B 17/29* | (2006.01) |
| *A61F 2/30* | (2006.01) |

(52) U.S. Cl.
CPC ........ *A61F 2/0045* (2013.01); *A61B 17/0625* (2013.01); *A61L 31/16* (2013.01); *A61B 17/42* (2013.01); *A61B 2017/2926* (2013.01); *A61F 2002/30062* (2013.01); *A61F 2002/30617* (2013.01); *A61F 2210/0004* (2013.01); *A61F 2250/0067* (2013.01); *A61F 2250/0097* (2013.01); *A61L 2300/00* (2013.01)

(58) Field of Classification Search
CPC ........ A61F 2/00; A61F 2/0004; A61F 2/0031; A61F 2/0036; A61F 2/0045; A61F 2/0063; A61B 2017/00805
See application file for complete search history.

(56) References Cited

U.S. PATENT DOCUMENTS

| | | | | |
|---|---|---|---|---|
| 2002/0028980 A1* | 3/2002 | Thierfelder | ...... | A61B 17/00234 600/37 |
| 2008/0021265 A1* | 1/2008 | Garbin | ............. | A61B 17/06109 600/30 |
| 2008/0081945 A1* | 4/2008 | Toso | ..................... | A61F 2/0045 600/37 |

(Continued)

*Primary Examiner* — Charles A Marmor, II
*Assistant Examiner* — Thaddeus Cox
(74) *Attorney, Agent, or Firm* — Quarles & Brady LLP

(57) ABSTRACT

An implantable medical device and surgical instrument for use during a procedure for treatment of vaginal vault prolapse. The invention also includes an instrument which allows the pieces of the suspension material to be attached to each other and enables the appropriate suspension of the vaginal apex from the anterior part of the sacrum. The device and method permit the performance of a sacrocolpopexy by accessing the sacrum and vaginal tissues via the vaginal orifice, thus avoiding the abdominal cavity completely.

19 Claims, 9 Drawing Sheets

(56) References Cited

U.S. PATENT DOCUMENTS

2008/0082177 A1\* 4/2008 Yang ............... A61F 2/0045
    623/23.75
2010/0305394 A1\* 12/2010 Rosenblatt ............ A61F 2/0063
    600/30

\* cited by examiner

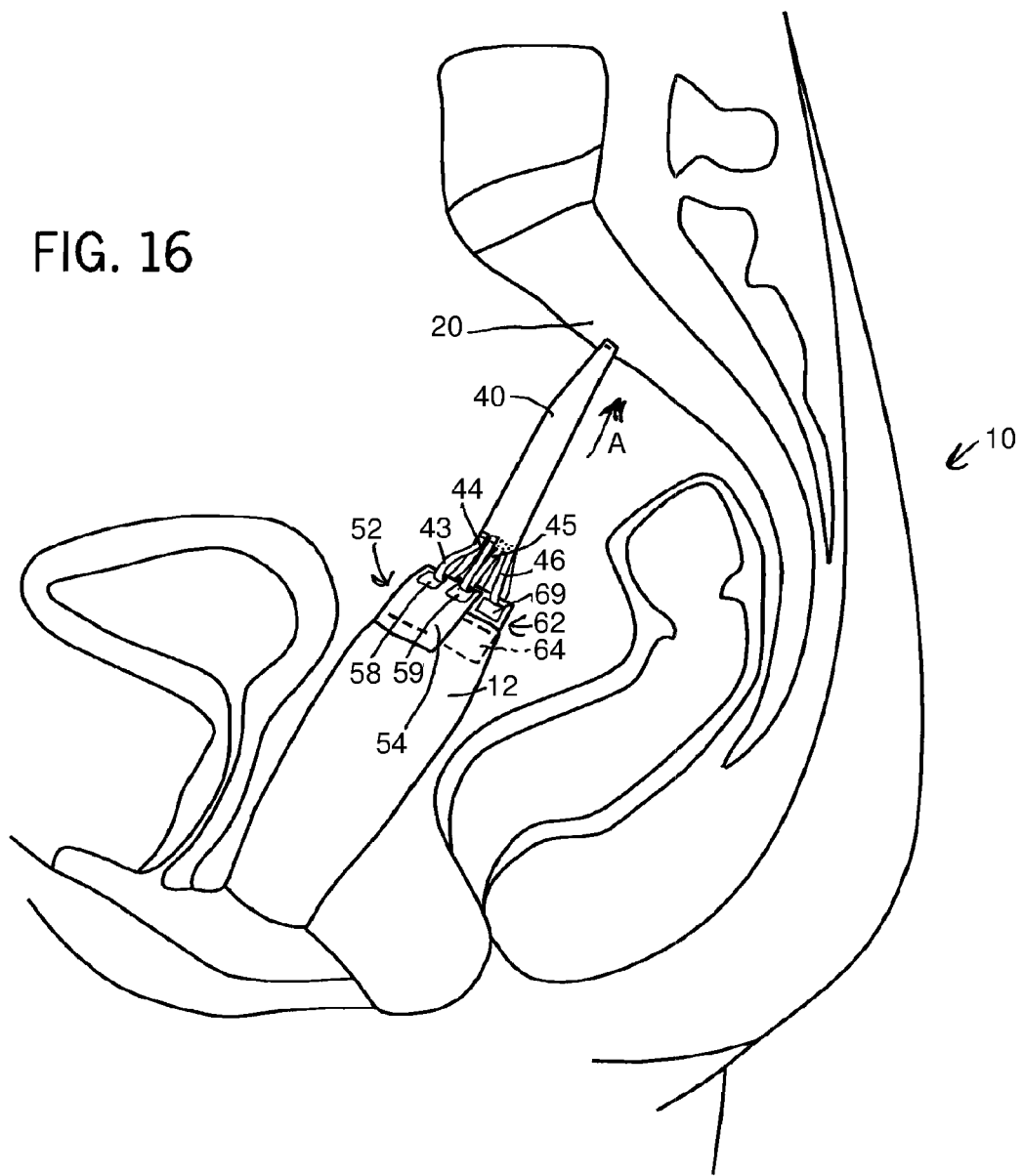

VAGINAL VAULT SUSPENSION DEVICE AND METHOD

CROSS-REFERENCE TO RELATED APPLICATIONS

This application is a continuation of U.S. patent application Ser. No. 13/497,181 filed Mar. 20, 2012, now U.S. Pat. No. 9,333,064, which represents the US National Stage of International Application PCT/US2010/049308 filed Sep. 17, 2010, which claims priority to U.S. Provisional Patent Application 61/245,149 filed Sep. 23, 2009 all of which are incorporated by reference herein in their entirety for all purposes.

STATEMENT REGARDING FEDERALLY SPONSORED RESEARCH

Not applicable.

FIELD OF THE INVENTION

The invention relates to an implantable medical device and a surgical instrument for using the device in a procedure for the treatment of pelvic organ prolapse. The invention enables a sacrocolpopexy to be performed via a vaginal incision.

BACKGROUND OF THE INVENTION

Pelvic organ prolapse is a common medical condition, affecting almost half of women over the age of 50. (See, Subak et al., "Cost Of Pelvic Organ Prolapse Surgery In The United States", *Obstet Gynecol.* 2001; 98(4):646-651.) As the population in the United States ages, there will be an increasing number of women who require treatment for this condition. This medical condition results in lifestyle restriction, social limitations, sexual dysfunction, and pain, but can also lead to more critical conditions such as urinary retention, urinary tract infection, and sepsis.

For over a century, gynecologists have devised reconstructive pelvic surgeries to address this problem. The gold standard for the repair of severe prolapse (vaginal vault prolapse) is the sacrocolpopexy. (See, Ganatra et al., "The Current Status Of Laparoscopic Sacrocolpopexy: A Review", *Eur Urol.* 2009. See, also, U.S. Pat. No. 6,592, 515.) This procedure suspends the apex of the vagina by affixing a Y-shaped piece of synthetic mesh to the anterior and posterior vaginal walls and suspending this from a strong ligament on the anterior part of the sacrum. This procedure is typically performed via a laparoscopic approach, entering the abdominal cavity to access the sacrum and vaginal tissues, both of which are retroperitoneal (behind the lining of the abdominal cavity). In some subjects (obese patients and individuals with severe abdominal adhesions from multiple prior surgeries), the laparoscopic approach is not possible, and a larger abdominal incision is required.

Vaginal surgery is another common route of repair for pelvic organ prolapse, but the sacrocolpopexy has not been performed via a vaginal incision due to technical constraints. Other surgical repairs performed vaginally have lower success rates. (See, Maher et al., "Surgical Management Of Pelvic Organ Prolapse In Women: A Short Version Cochrane Review", *Neurourol Urodyn.* 2008, 27(1):3-12.)

Therefore, there is a need for a surgical device and method which permit the performance of a sacrocolpopexy by accessing the sacrum and vaginal tissues via the vaginal orifice, thus avoiding the abdominal cavity completely.

SUMMARY OF THE INVENTION

The present invention satisfies the foregoing needs by providing devices and surgical methods that allow for a vaginal approach to a sacrocolpopexy. The availability of a vaginal approach for the sacrocolpopexy can be advantageous to patients who cannot undergo a laparoscopic procedure, precisely because the vaginal approach does not require intraabdominal dissection, but only retroperitoneal dissection. This approach avoids many of the surgically risky or technically challenging problems of abdominal or laparoscopic entry in the obese patient or the patient with significant intraabdominal adhesive disease. Vaginal surgery is effectively a natural orifice surgery, resulting in an even less invasive approach than laparoscopy or robotic surgery.

At least four challenges to the accomplishment of the vaginal sacrocolpopexy were identified. They include the visualization of the suspension material attachment sites when performing the procedure through a small opening in the vagina, performing a retroperitoneal dissection via the vaginal approach to the level of the sacrum, affixing the suspension material to the sacrum through the vaginal incision, and suspending the vagina while approaching from the most dependent portion of the prolapse.

With these challenges in mind, a solution was developed including a specialized configuration of suspension material (an example suspension material is polypropylene mesh), the development of the retroperitoneal space extending from a vaginal incision to the sacral promontory, a method for affixing the mesh to the anterior part of the sacrum, and an instrument allowing the suspension of the vaginal walls from the sacral promontory.

The invention includes a multipart suspension device. In one form of the suspension device, one attachment part attaches to the anterior and posterior parts of the vaginal apex, and the other attachment part attaches to anterior part of the sacrum. The two attachment parts are capable of being attached together during the procedure in a manner which permits appropriate adjustment of tension. The invention also includes an instrument which allows the pieces of the suspension material to be attached to each other and enables the appropriate suspension of the vaginal apex from the anterior part of the sacrum. The implantable device and instrument can be supplied as a sterile surgical kit. In another form of the suspension device, one attachment part attaches to the anterior part of the vaginal apex, another separate attachment part attaches to the posterior part of the vaginal apex, and another separate attachment part attaches to anterior part of the sacrum.

In one version of a surgical procedure according to the invention, the surgeon can begin by making a 3-4 centimeter incision at the apex of the vaginal vault, entering the retroperitoneal space at the level of the rectovaginal septum. Then, using $CO_2$ insufflation or blunt dissection, the anterior part of the sacrum, just distal to the sacral promontory, can be visualized and cleared of overlying tissue. Using a laparoscopic needle driver (or direct suture device) sutures can then be placed in the ligament overlying the anterior part of the sacrum. These can be attached to the apical portion of the suspension material, and using a pulley stitch, the suspension material can be affixed to the sacrum.

The configuration of the suspension material is designed to allow placement of the mesh on the anterior and posterior vaginal walls, between the peritoneal layer and the endopelvic fascia, while maintaining visualization of the suspension material affixed to the sacral promontory. After and dissecting away the overlying peritoneal lining along the anterior and posterior vaginal walls, the second portion of the suspension material can be attached to the anterior and posterior aspects of the vagina.

The end flaps of the suspension material affixed to the sacrum can then be looped through slots in the vaginal portions of the material. By affixing the distal end of the flap to its proximal end, the vaginal portions of the material can be suspended from the sacral promontory. The optimal level of suspension can be permitted by affixing the flap to itself (or to a distal section of the suspension material) to form a loop at the correct level. Once appropriate suspension is achieved, a device containing a loop of permanent suture can be deployed to permanently attach the vaginal portions of the suspension material to the sacral portion. The single incision at the apex of the vaginal can then be closed, burying the suspension device beneath the mucosa of the vaginal apex.

Currently available devices are not suitable for the performance of a sacrocolpopexy from a vaginal approach. The typical "Y-shaped" mesh used in a sacrocolpopexy would obstruct the view of the sacrum during a vaginal procedure, and could not be used to adequately provide suspension of the vagina. During a laparoscopic approach, the vagina is suspended from the sacral promontory by pushing up on the vagina using a vaginal probe, viewing this laparoscopically, and trimming and attaching the suspension device to the sacrum as the final part of the procedure. This is not possible to do when performing from a vaginal approach, as such a probe would further obscure the operative site. Another advantage to a vaginal approach for this procedure is to apply the "gold standard" surgical repair for prolapse in an approach that is even more minimally invasive than a laparoscopic approach, making this procedure available to patients who might not have been eligible for it otherwise.

Existing solutions permit the performance of sacrocolpopexy via abdominal, laparoscopic and robotic (e.g., Da Vinci®) approaches. The present invention is a multipart device allowing for the performance of the sacrocolpopexy from a vaginal approach. The multipart suspension material is configured to allow visualization of the sacrum through a vaginal opening, while providing the ability to suspend the vaginal apex from the sacrum. The instrument allows tensioning of the mesh, and can also be used to measure the amount of tension placed on the suspension, providing more precise repair.

In one aspect of the invention, there is provided a device for treating pelvic organ prolapse in a patient. The device includes a first flexible attachment part including a base section and a flap extending away from the base section wherein the base section is suitable for affixing to the sacrum or tissue adjacent the sacrum of the patient. The device also includes a second separate flexible attachment part including an opening and a slot adjacent the opening, wherein the second attachment part is suitable for affixing to the pelvic organ of the patient. The first attachment part and the second attachment part are dimensioned such that the flap of the first attachment part can be looped though the opening and the slot in the second attachment part and the flap can be attached to the first attachment part thereby suspending the pelvic organ from the sacrum or the tissue adjacent the sacrum of the patient.

In another aspect of the invention, there is provided a device for treating pelvic organ prolapse in a patient. The device includes a first flexible attachment part including a base section and a slot wherein the base section is suitable for affixing to the sacrum or tissue adjacent the sacrum of the patient. The device also includes a second separate flexible attachment part including an opening and at least one flap wherein the second attachment part is suitable for affixing to the pelvic organ of the patient. The first attachment part and the second attachment part are dimensioned such that the flap of the second attachment part can be looped though the slot in the first attachment part and the flap can be attached to the second attachment part thereby suspending the pelvic organ from the sacrum or the tissue adjacent the sacrum of the patient.

In yet another aspect of the invention, there is provided a device for treating pelvic organ prolapse in a patient. The device includes a first flexible attachment part including a base section, a first flap extending away from the base section, and a second flap extending away from the base section wherein the base section is suitable for affixing to the sacrum or tissue adjacent the sacrum of the patient. The device also includes a second separate flexible attachment part including a slot wherein the second attachment part is suitable for affixing to the pelvic organ of the patient. The device also includes a third separate flexible attachment part including a slot wherein the third attachment part is suitable for affixing to the pelvic organ of the patient. The first attachment part and the second attachment part and the third attachment part are dimensioned such that the first flap of the first attachment part can be looped though the slot in the second attachment part and the first flap can be attached to the first attachment part and such that the second flap of the first attachment part can be looped though the slot in the third attachment part and the second flap can be attached to the first attachment part thereby suspending the pelvic organ from the sacrum or the tissue adjacent the sacrum of the patient.

In still another aspect of the invention, there is provided a device for treating pelvic organ prolapse in a patient. The device includes a first flexible attachment part including a base section, a first slot and a second slot wherein the base section is suitable for affixing to the sacrum or tissue adjacent the sacrum of the patient. The device also includes a second separate flexible attachment part including a flap wherein the second attachment part is suitable for affixing to the pelvic organ of the patient. The device also includes a third separate flexible attachment part including a flap wherein the second attachment part is suitable for affixing to the pelvic organ of the patient. The first attachment part and the second attachment part and the third attachment part are dimensioned such that the flap of the second attachment part can be looped though the first slot in the first attachment part and the flap of the second attachment part can be attached to the second attachment part and such that the flap of the third attachment part can be looped though the slot in the first attachment part and the flap of the third attachment part can be attached to the third attachment part thereby suspending the pelvic organ from the sacrum or the tissue adjacent the sacrum of the patient.

In yet another aspect of the invention, there is provided a surgical kit for treating pelvic organ prolapse in a patient. The kit includes a first flexible attachment part including a base section suitable for affixing to the sacrum or tissue adjacent the sacrum of the patient, a second separate flexible attachment part suitable for affixing to the pelvic organ of the patient, and an instrument for attaching the first attachment part and the second attachment part. The instrument includes a holder for holding a surface section of the first attachment part or a surface section the second attachment part in adjacent or touching relationship with a second surface section of the first attachment part, and the instrument includes an attachment mechanism for affixing the surface section of the first attachment part or the surface section the second attachment part to the second surface section of the first attachment part.

In still another aspect of the invention, there is provided a surgical instrument for attaching a first flexible attachment part and a second separate flexible attachment part. The instrument includes a holder for holding a surface section of the first attachment part or a surface section the second attachment part in adjacent or touching relationship with a second surface section of the first attachment part, and an attachment mechanism for affixing the surface section of the first attachment part or the surface section the second attachment part to the second surface section of the first attachment part.

In yet another aspect of the invention, there is provided method for treating pelvic organ prolapse in a patient. In the method, an incision is formed in a vaginal wall. A first attachment part is passed through the incision, and the first attachment part is affixed to the sacrum or tissue adjacent the sacrum of the patient. A second attachment part is affixed to a wall of the pelvic organ, and the second attachment part is affixed to the first attachment part thereby suspending the pelvic organ from the sacrum or the tissue adjacent the sacrum.

In various versions of the invention, the first attachment part and/or the second attachment part and/or the third attachment part can comprise a mesh material such as polyethylene, polypropylene, nylons, poly-L-lactide, polyethylene glycol, polyesters, and any combination thereof. The first attachment part and/or the second attachment part and/or the third attachment part can comprise a bioactive agent such as one or more of cells, drugs, precursors, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics. The first attachment part and/or the second attachment part and/or the third attachment part can comprise a section treated with a dye to aid in visualization during surgery.

These and other features, aspects, and advantages of the present invention will become better understood upon consideration of the following detailed description, drawings, and appended claims.

BRIEF DESCRIPTION OF THE DRAWINGS

FIG. 16 is a schematic side view of a human patient showing the suspension devices of FIGS. 4 and 5 in the final position in which the vaginal walls are suspended from the sacral promontory.

Like reference numerals will be used to refer to like parts from Figure to Figure in the following description of the drawings.

DETAILED DESCRIPTION OF THE INVENTION

Figure 1:
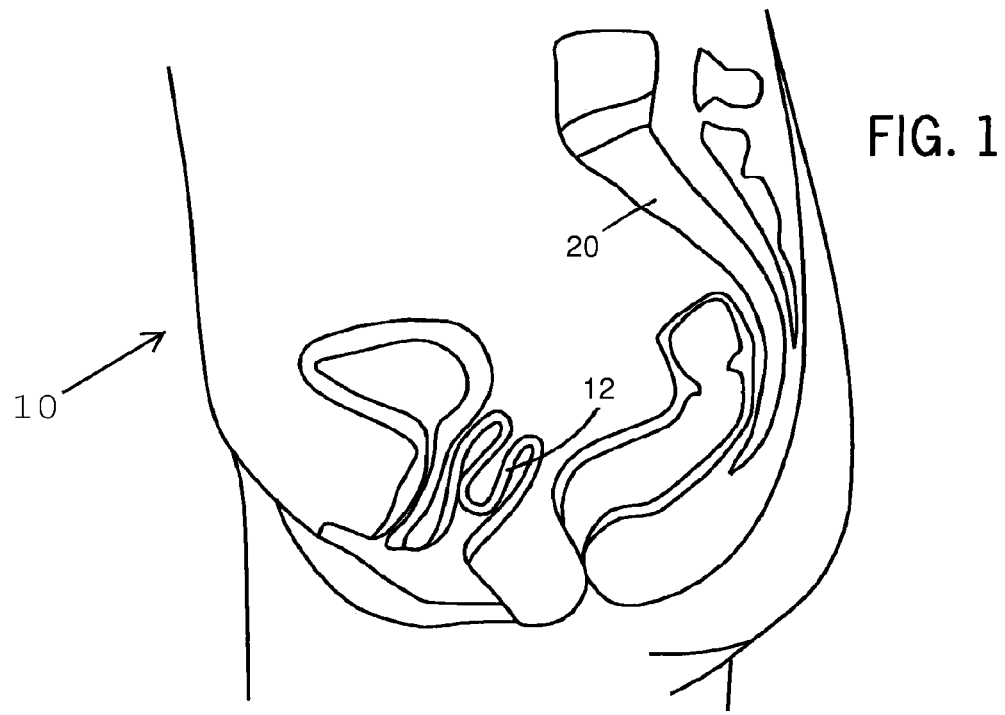
FIG. 1 is a schematic side view of a human patient having a prolapsed vagina.
Figure 2:
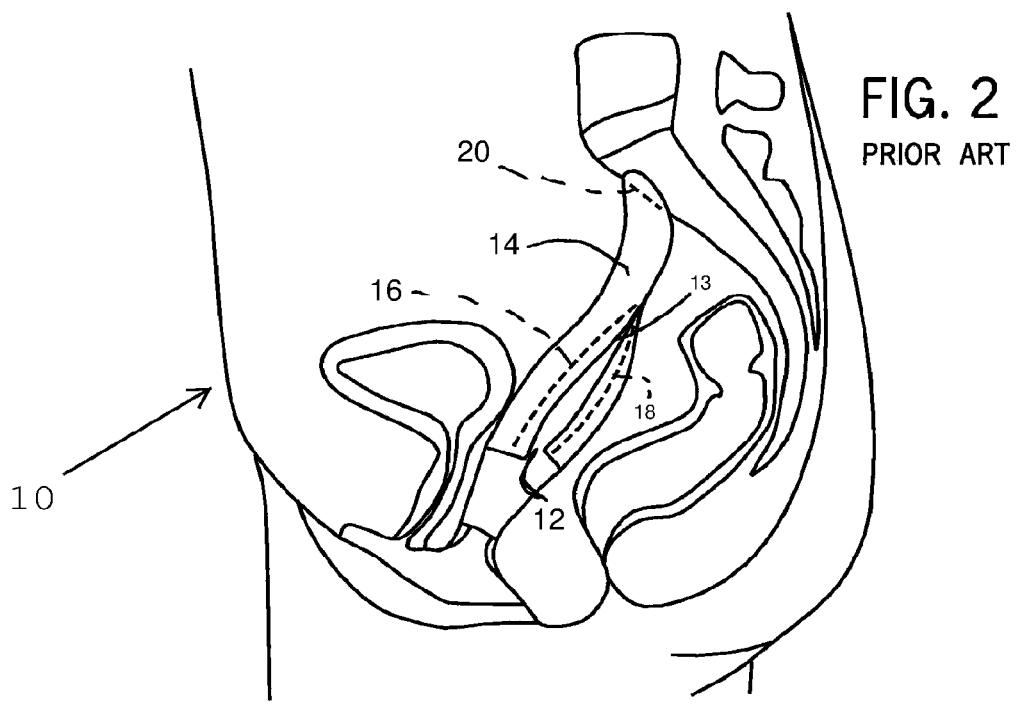
FIG. 2 shows a schematic side view of a human patient after a prior art device has been implanted for treatment of a prolapsed vagina.

Referring to FIG. 1, there is shown a schematic side view of a human patient 10 having a prolapsed vagina 12. In the prior art sacrocolpopexy method shown in FIG. 2, the apex 13 of the vagina 12 has been suspended by affixing a Y-shaped article 14 of synthetic mesh to the anterior vaginal wall 16 and posterior vaginal wall 18 and suspending the article 14 from a strong ligament on the anterior part of the sacrum 20. This prior art procedure is typically performed via a laparoscopic approach, entering the abdominal cavity to access the sacrum and vaginal tissues, both of which are retroperitoneal (behind the lining of the abdominal cavity). More details on an example version of the prior art method of FIG. 2 can be found in U.S. Pat. No. 6,592,515.

Figure 3:
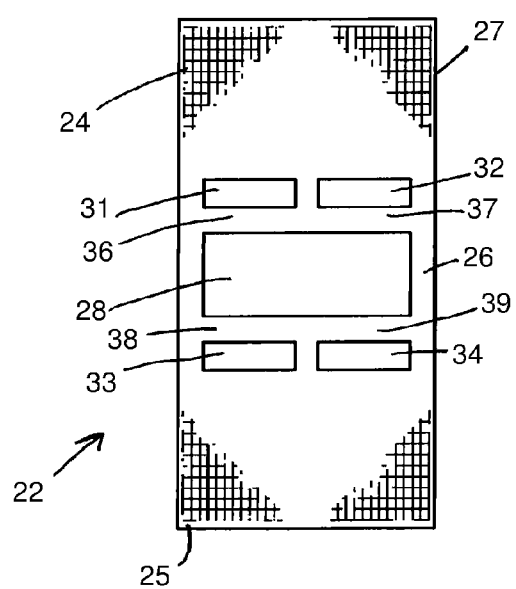
FIG. 3 is a top view of one attachment part of a suspension device according to the invention, the attachment part of FIG. 3 being suitable for attaching to the anterior and posterior sections of the vaginal apex in a surgical method according to the invention.

Turning now to FIG. 3, there is shown a top view of one attachment part 22 of a suspension device used in a method for treating pelvic organ prolapse according to the invention. The attachment part 22 includes a first end section 24, a second end section 25, and an intermediate section 26 between the first end section 24 and the second end section 25. In the example version shown, the attachment part 22 has a rectangular perimeter 27. The intermediate section 26 has a central rectangular opening 28. The intermediate section 26 also has a first slot 31 and a second slot 32 on one side of the opening 28, and also has a third slot 33 and a fourth slot 34 on an opposite side of the opening 28. A strip 36 of material is formed between the first slot 31 and the opening 28. A strip 37 of material is formed between the second slot 32 and the opening 28. A strip 38 of material is formed between the third slot 33 and the opening 28. A strip 39 of material is formed between the fourth slot 34 and the opening 28. When used in a surgical method according to the invention, the first end section 24 of the attachment part 22 is suitable for attaching to the outer surface of the anterior vaginal wall 16 near the apex 13 of the vagina 12, and the second end section 25 of the attachment part 22 is suitable for attaching to the outer surface of the posterior vaginal wall 18 near the apex 13 of the vagina 12. Use of the attachment part 22 in a surgical method according to the invention is explained further below.

Figure 4:
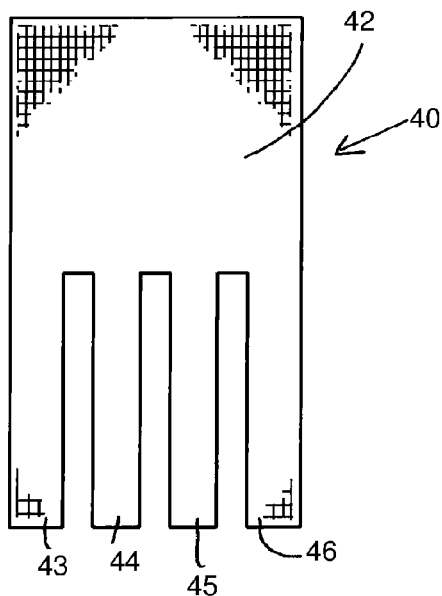
FIG. 4 is a top view of another attachment part of a suspension device according to the invention, the attachment part of FIG. 4 being suitable for attaching to the anterior of the sacrum in a surgical method according to the invention.

Referring now to FIG. 4, there is shown a top view of an attachment part 40 of a suspension device according to the invention. The attachment part 40 includes a base section 42 and four spaced apart flaps 43, 44, 45, 46 that extend away from the base section 42 of the attachment part 40. When used in a surgical method according to the invention, the base section 42 of the attachment part 40 is suitable for attaching to the anterior of the sacrum 20. Use of the attachment part 40 in a surgical method according to the invention is explained further below.

Figure 5:
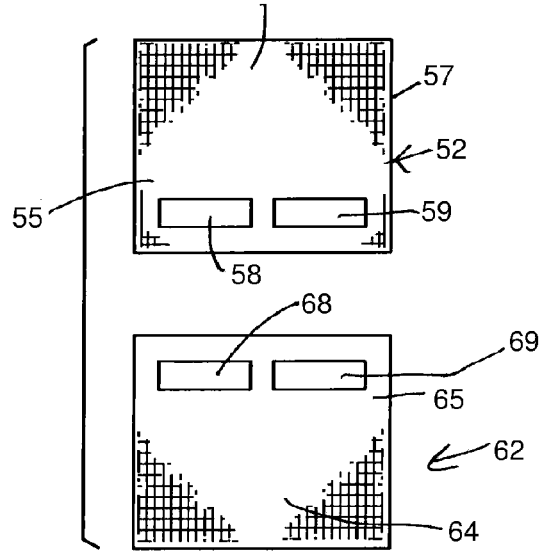
FIG. 5 is a top view of two attachment parts of a suspension device according to another embodiment of the invention, the attachment parts of FIG. 5 being suitable for attaching to the anterior and posterior sections of the vaginal apex respectively in another surgical method according to the invention.

Looking now at FIG. 5, there is shown a top view of a first attachment part 52 of another version of a suspension device according to the invention. The first attachment part 52 includes a first end section 54, and a second end section 55. In the example version shown, the first attachment part 52 has a rectangular perimeter 57. The second end section 55 has a first slot 58 and a second slot 59. When used in a surgical method according to the invention, the first end section 54 of the first attachment part 52 is suitable for attaching to the outer surface of the anterior vaginal wall 16 near the apex 13 of the vagina 12, or to the outer surface of the posterior vaginal wall 18 near the apex 13 of the vagina 12. Use of the first attachment part 52 in a surgical method according to the invention is explained further below.

Still looking at FIG. 5, there is shown a top view of a second attachment part 62 of another version of a suspension device according to the invention. The second attachment part 62 includes a first end section 64, and a second end section 65. In the example version shown, the second attachment part 62 has a rectangular perimeter 67. The second end section 65 has a first slot 68 and a second slot 69. When used in a surgical method according to the invention, the first end section 64 of the second attachment part 62 is suitable for attaching to the outer surface of the anterior vaginal wall 16 near the apex 13 of the vagina 12, or to the outer surface of the posterior vaginal wall 18 near the apex 13 of the vagina 12. Use of the second attachment part 62 in a surgical method according to the invention is explained further below.

Each of the attachment part 22, the attachment part 40, the first attachment part 52, and the second attachment part 62 preferably comprises a mesh material with pores that afford tissue ingrowth and resist infection. (FIGS. 3-5 show mesh regions at different sections of the attachment part 22, the attachment part 40, the first attachment part 52, and the second attachment part 62 for the sake of clarity.) The mesh material may comprise any section or all sections of the attachment part 22, the attachment part 40, the first attachment part 52, and the second attachment part 62.) The mesh material may comprise woven, knitted or inter-linked filaments or fibers that form multiple junctions. The junctions may be formed via weaving, bonding, ultrasonic welding, knitting or other junction forming techniques. The flexible mesh material provides for elasticity in both lateral and longitudinal directions. Non-limiting examples of materials for forming the mesh material include polyethylene, polypropylene, nylons, poly-L-lactide, polyethylene glycol, polyesters, and any combination of these materials. As a non-limiting example, the mesh material comprises polypropylene filaments, such as a 75 micron weave. Non-synthetic materials such as grafts and collagen may also be suitable for forming the attachment part 22, the attachment part 40, the first attachment part 52, and the second attachment part 62.

Each of the attachment part 22, the attachment part 40, the first attachment part 52, and the second attachment part 62 may also include one or more bioactive agents associated with the mesh material through a process such as coating. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, cells, drugs, precursors, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics.

Optionally, a dye may be coated on one or more surface sections of any of the attachment part 22, the attachment part 40, the first attachment part 52, and the second attachment part 62. The dye provides the surgeon with a visual indicator to aid in properly orienting the attachment part 22, the attachment part 40, the first attachment part 52, and the second attachment part 62 at the target site within the patient. Various different colors of dyes may be used for the attachment part 22, the attachment part 40, the first attachment part 52, and the second attachment part 62. Different colors of dyes may be used on different sections of the same part to provide a visual indicator to aid in properly orienting the attachment part 22, the attachment part 40, the first attachment part 52, and the second attachment part 62 at the target site within the patient.

Figure 6:
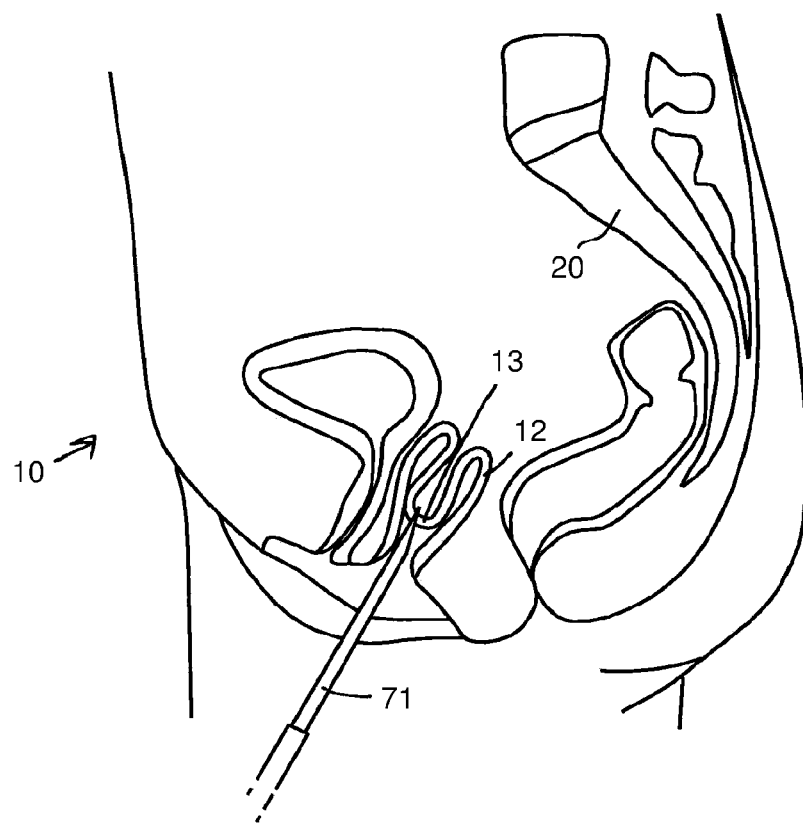
FIG. 6 shows a schematic side view of a human patient in a step of a surgical method according to the invention wherein an incision is made at the apex of the prolapsed vagina.
Figure 7:
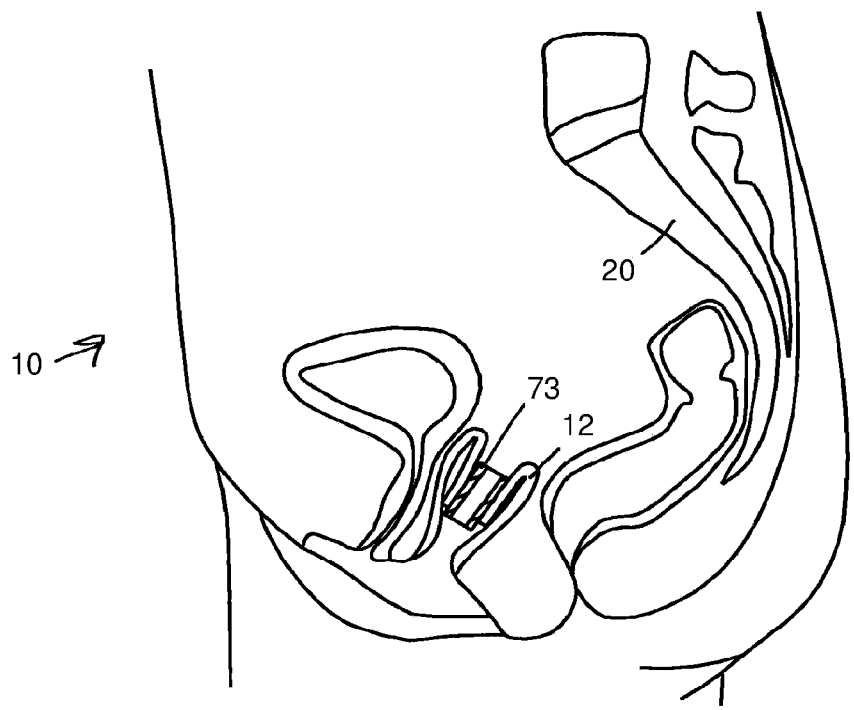
FIG. 7 shows a schematic side view of a human patient in a step of a surgical method according to the invention wherein a trocar sleeve is placed in the incision made at the apex of the prolapsed vagina.

Turning now to FIGS. 6-15, use of the attachment part 22 and the attachment part 40 in a surgical procedure according to the invention for the treatment of vaginal vault prolapse can be detailed further. In the version of a surgical procedure according to the invention shown, the surgeon can begin by making a 3-4 centimeter incision with a surgical tool 71 at the apex 13 of the vaginal vault 12, entering the retroperitoneal space at the level of the rectovaginal septum. This is shown in FIG. 6. The surgeon can insert a trocar sleeve 73 in the incision as shown in FIG. 7. Then, using $CO_2$ insufflation or blunt dissection, the anterior part of the sacrum 20, just distal to the sacral promontory, can be visualized and cleared of overlying tissue.

Figure 8:
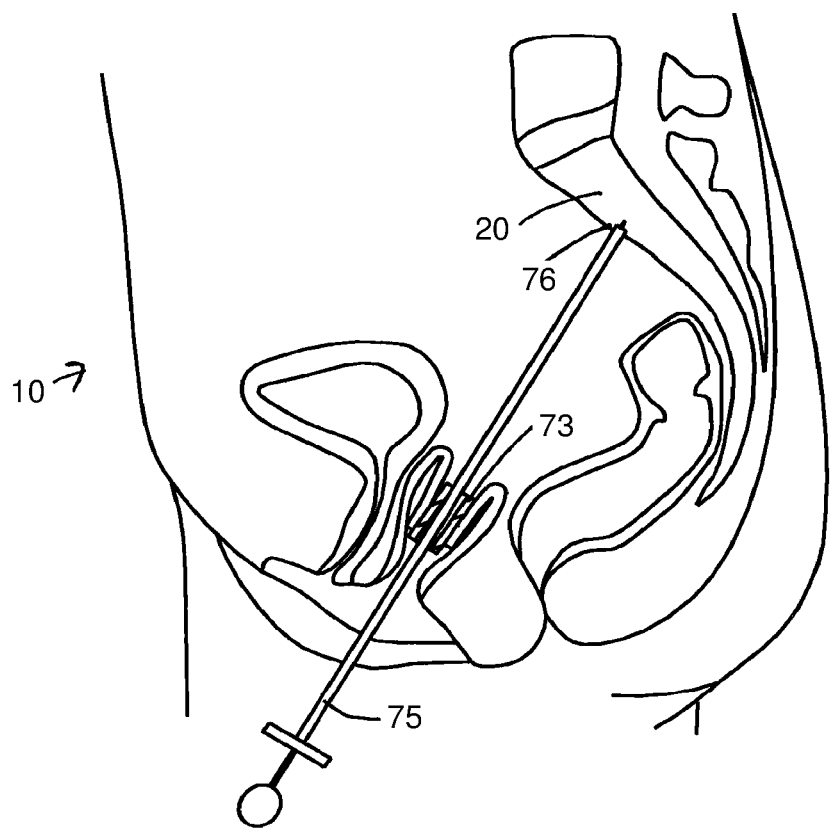
FIG. 8 shows a schematic side view of a human patient in a step of a surgical method according to the invention wherein a laparoscopic suture capturing device is placing a suture in the ligament overlying the anterior part of the sacrum.

Looking at FIG. 8, a laparoscopic needle driver, or direct suture device, or suture capturing device 75 can be inserted through trocar sleeve 73 and can be used to place sutures in the ligament overlying the anterior part of the sacrum 20. The position of the suture is indicated at 76 in FIG. 8. One example suture capturing device is described in U.S. Pat. No. 6,048,351. The suture capturing device of this patent has been sold under the trademark "Capio". Another example suturing device can be found in U.S. Pat. No. 6,071,289. The suture capturing device of this patent can be advantageous as it can suture transverse to the longitudinal axis of the device.

Figure 9:
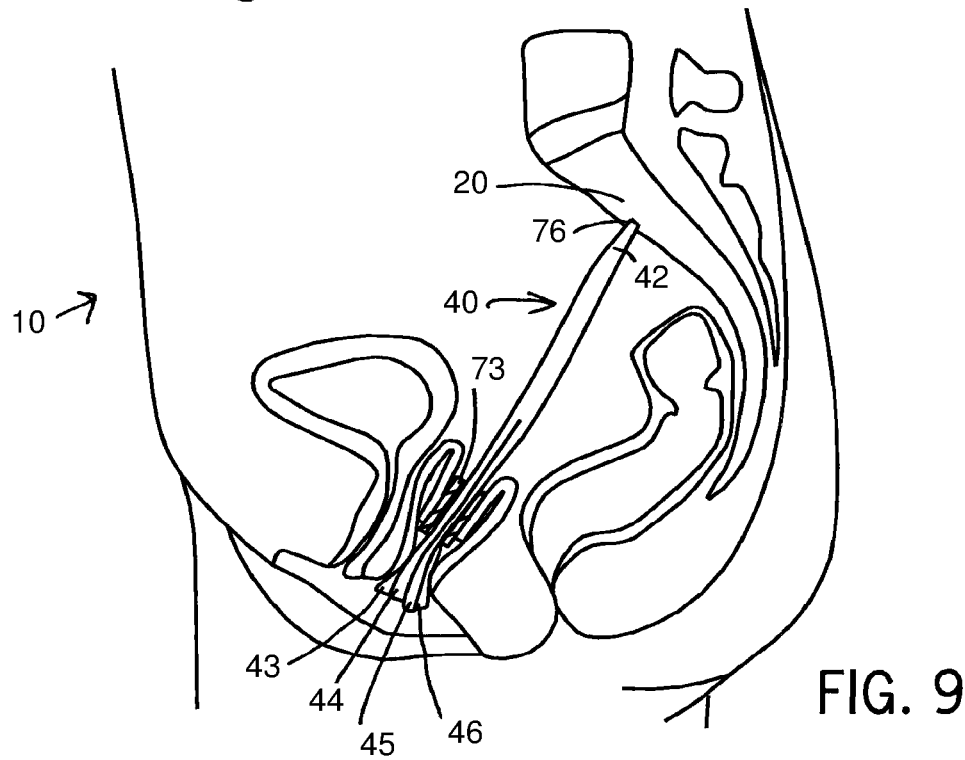
FIG. 9 shows a schematic side view of a human patient in a step of a surgical method according to the invention wherein the suspension device of FIG. 4 has been affixed to the ligament overlying the anterior part of the sacrum.
Figure 10:
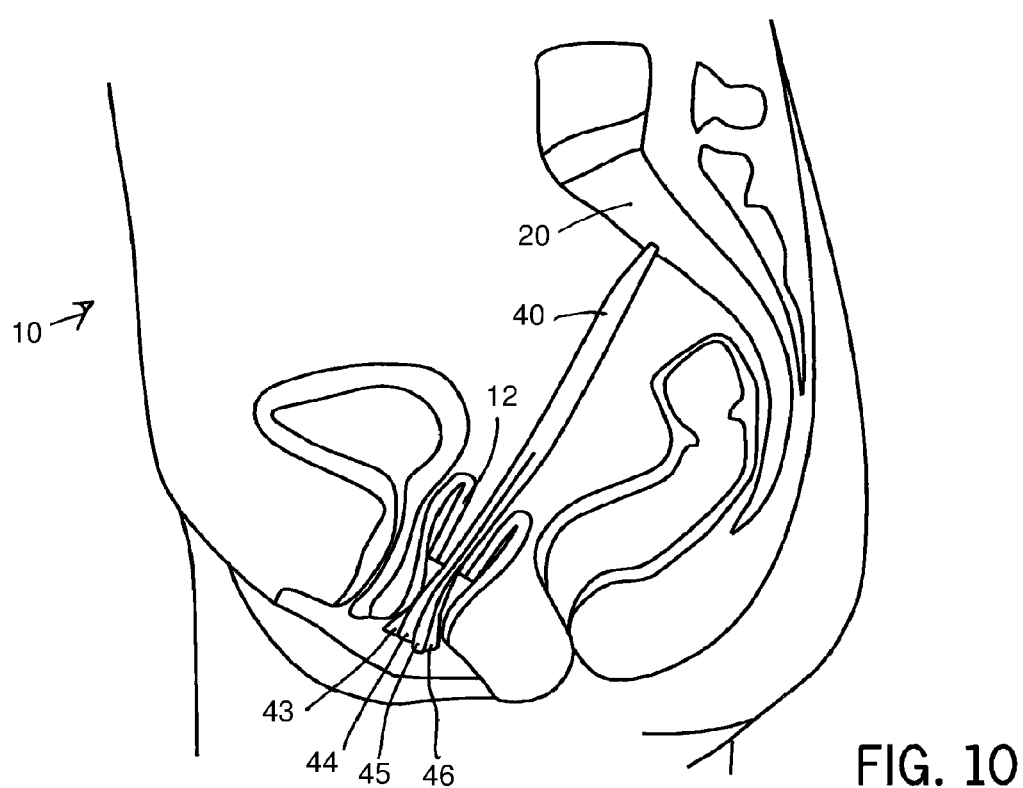
FIG. 10 shows a schematic side view of a human patient in a step of a surgical method according to the invention wherein the trocar sleeve has been removed from the incision in the vagina.

Referring now to FIG. 9, the sutures in the ligament overlying the anterior part of the sacrum 20 can be attached to the apical portion of the base section 42 of the attachment part 40, and using a pulley stitch, the base section 42 of the attachment part 40 can be affixed to the sacrum 20. After the base section 42 of the attachment part 40 is affixed to the sacrum 20, the four spaced apart flaps 43, 44, 45, 46 of the attachment part 40 extend through the trocar sleeve 73, which may be removed as shown in FIG. 10.

Figure 11:
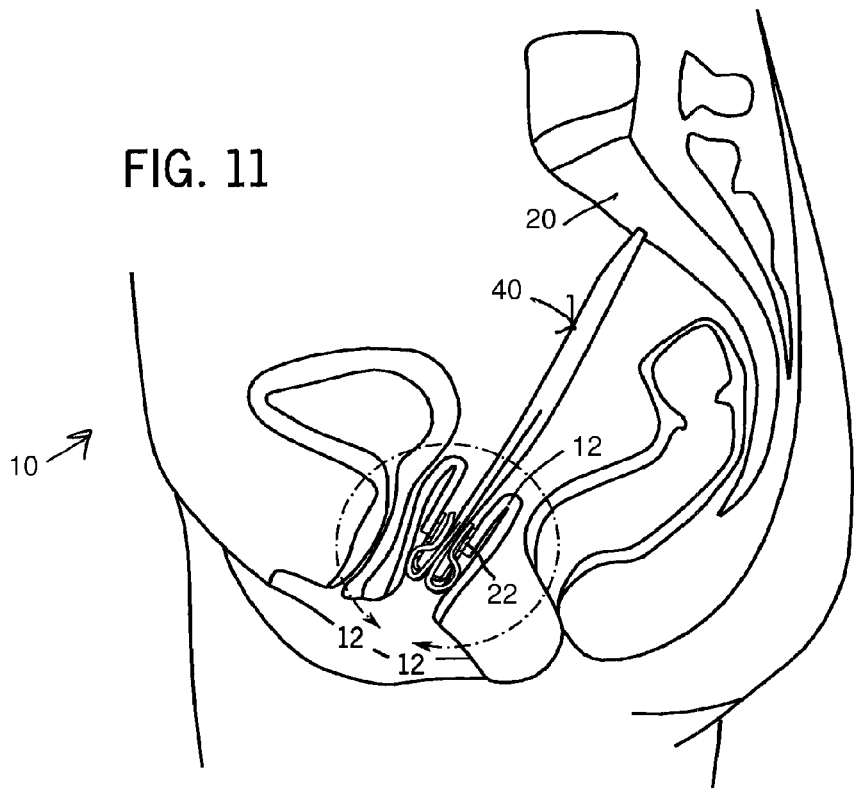
FIG. 11 shows a schematic side view of a human patient in a step of a surgical method according to the invention wherein ends of the suspension device of FIG. 3 have been affixed to the anterior and posterior sections of the vaginal apex and end flaps of the suspension device of FIG. 4 have been inserted in slots in the suspension device of FIG. 3.
Figure 12:
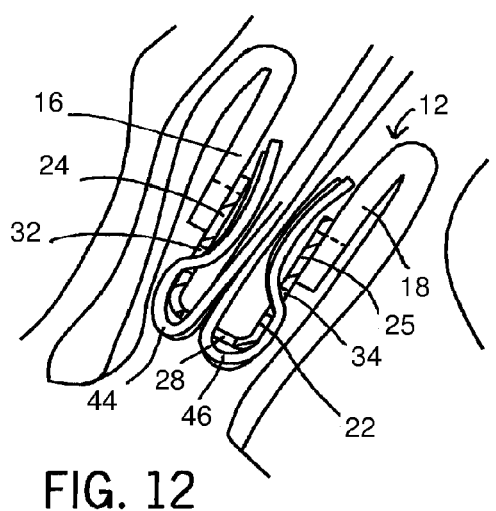
FIG. 12 is a detailed view taken along line 12-12 of FIG. 11.
Figure 13:
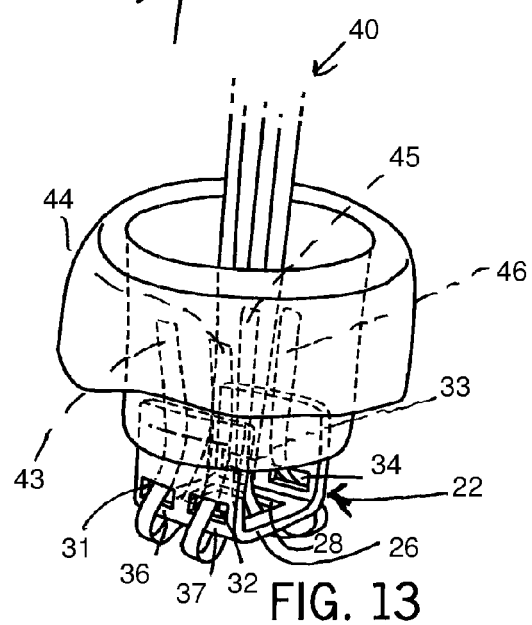
FIG. 13 is a perspective view of the surgical step shown in FIGS. 11 and 12 wherein end flaps of the suspension device of FIG. 4 have been inserted in slots in the suspension device of FIG. 3.

Turning now to FIGS. 11-13, the surgeon attaches the first end section 24 of the attachment part 22 to the outer surface of the anterior vaginal wall 16 near the apex 13 of the vagina 12, and attaches the second end section 25 of the attachment part 22 to the outer surface of the posterior vaginal wall 18 near the apex 13 of the vagina 12. (Because the vagina 12 in FIGS. 11-13 is prolapsed, the outer surface of the vagina 12 faces inward.)

Looking at FIG. 13, the surgeon arranges the four spaced apart flaps 43, 44, 45, 46 of the attachment part 40 as follows. The flap 43 is inserted downward through opening 28 of the attachment part 22 around the strip 36 of material and back up through the first slot 31 of the attachment part 22. Likewise, the flap 44 is inserted downward through opening 28 of the attachment part 22 around the strip 37 of material and back up through the second slot 32 of the attachment part 22. Likewise, the flap 45 is inserted downward through opening 28 of the attachment part 22 around the strip 38 of material and back up through the third slot 33 of the attachment part 22. Likewise, the flap 45 is inserted downward through opening 28 of the attachment part 22 around the strip 39 of material and back up through the fourth slot 34 of the attachment part 22.

Figure 14:
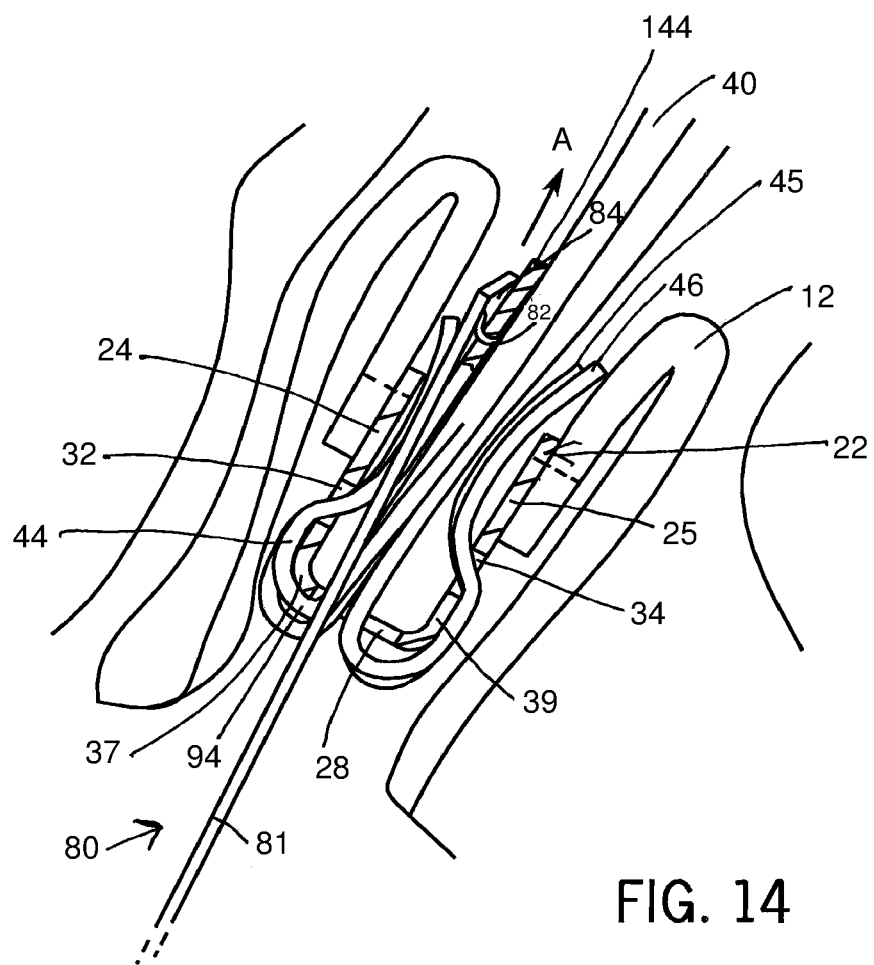
FIG. 14 is a schematic side view of a human patient in a step of a surgical method according to the invention wherein an end flap of the suspension device of FIG. 4 is affixed to itself (or to a distal section of the suspension material) to form a loop at the correct level.

Now, turning to FIG. 14, the surgeon uses an instrument 80 according to the invention for attaching the attachment part 22 and the attachment part 40. The instrument 80 includes a shaft 81 carrying a hook 82 for holding the flap 44 and an attachment mechanism 84. The instrument 80 includes a tension gauge for measuring a tension on the hook 82 when the hook 82 engages the mesh of the distal end 144 of the flap 44 and is moved in direction A of FIG. 14. The tension gauge includes a load cell coupled to the hook 82 for measuring the tension. The attachment mechanism 84 can be a stapling or clipping device. The attachment mechanism 84 can be a suture capturing device. The attachment mechanism 84 can be a riveting device. The attachment mechanism 84 can be a heat welding device.

Still referring to FIG. 14, the surgeon first engages the flap 44 with the hook 82 of the instrument 80. As the surgeon moves the instrument 80 in direction A toward the sacrum, the lower loop end 94 of the flap 44 will exert an upward force in direction A on the strip 37 of material formed between the second slot 32 and the opening 28 of the attachment part 22. This causes the attachment part 22 to move in direction A. After continued movement in direction A, the attachment part 22 and attached vagina 12 will invert to the position shown in FIG. 15. Eventually, the vagina 12 will prevent further upward movement of the attached attachment part 22. At this time, the tension gauge will measure a tension on the hook 82 as the distal end 144 of the flap 44 is prevented from freely moving in direction A due to the restraining force of the strip 37 of material formed between the second slot 32 and the opening 28 of the attachment part 22. The tension gauge includes a suitable LED display that is in electrical communication by way of circuitry with the load cell such that the surgeon can view the tension on the distal end 144 of the flap 44 on the display.

When a suitable tension is reached, the distal end 144 of the flap 44 is sandwiched between the attachment mechanism 84 and the attachment part 40. The distal end 144 of the flap 44 can then be attached to the attachment part 40 by the attachment mechanism 84. For example, the attachment mechanism 84 can staple or clip together the distal end 144 of the flap 44 and the attachment part 40. Alternatively, the attachment mechanism 84 can attach a suture such that the distal end 144 of the flap 44 and the attachment part 40 can be sutured together. Alternatively, the attachment mechanism 84 can rivet together the distal end 144 of the flap 44 and the attachment part 40. Alternatively, the attachment mechanism 84 can heat weld together the distal end 144 of the flap 44 and the attachment part 40.

The method described above for attaching the distal end 144 of the flap 44 and the attachment part 40 can also be used to attach the distal ends of the flaps 43, 45, 46 to the attachment part 40. The flaps 43, 44, 45, 46 can be of sufficient length such that the flaps 43, 44, 45, 46 do not fall out of slots 31, 32, 33, 34 when the attachment part 22 moves in direction A of FIG. 4. Extra length for the flaps 43, 44, 45, 46 that remains after attachment to the attachment part 40 can be removed by the surgeon.

Figure 15:
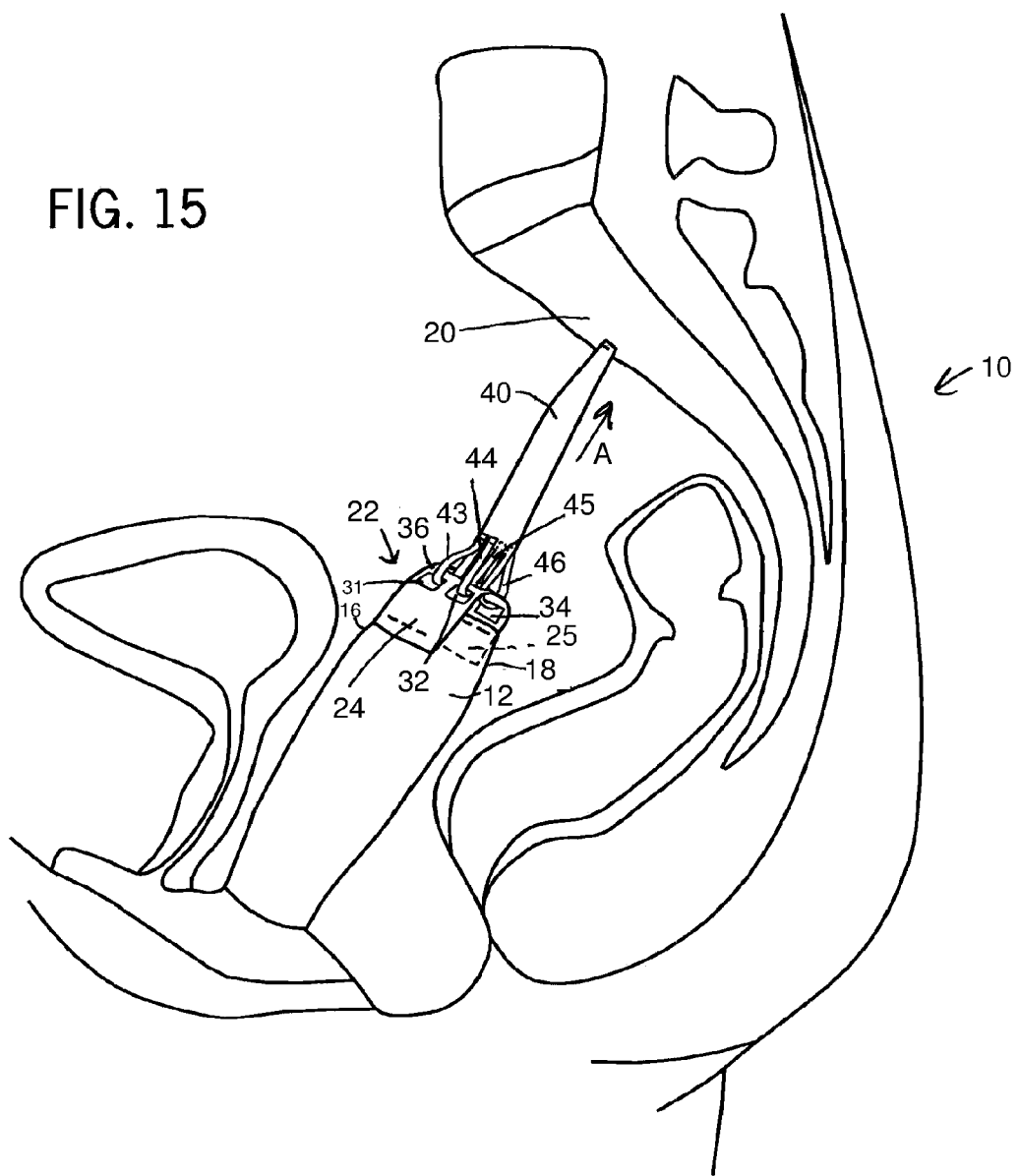
FIG. 15 is a schematic side view of a human patient showing the suspension devices of FIGS. 3 and 4 in the final position in which the vaginal walls are suspended from the sacral promontory.

Referring now to FIG. 15, the attachment part 22 and the attachment part 40 are shown in the fully assembled implanted configuration. The apical portion of the base section 42 of the attachment part 40 is attached to the ligament overlying the anterior part of the sacrum 20. Alternatively, the apical portion of the base section 42 of the attachment part 40 can be attached directly to the anterior part of the sacrum 20 using, for example, a tack. The first end section 24 of the attachment part 22 has been attached to the outer surface of the anterior vaginal wall 16 near the apex of the vagina 12, and the second end section 25 of the attachment part 22 has been attached to the outer surface of the posterior vaginal wall 18 near the apex of the vagina 12.

Still referring to FIG. 15, the flap 43 of the attachment part 40 has been inserted downward through opening 28 of the attachment part 22 around the strip 36 of material and back up through the first slot 31 of the attachment part 22. The distal end of the flap 43 has been attached to the attachment part 40. Likewise, the flaps 44, 45, 46 have been attached to the attachment part 40 as described above. The loops formed by the flaps 43, 44, 45, 46 exert a force in direction A on the attachment part 22, which is attached to the vagina 12 as described above and shown in FIG. 15. This suspends the vagina 12 from the sacrum 20 thereby treating prolapse.

The surgical method can also be performed using the attachment parts 52, 62 and the attachment part 40. Referring now to FIG. 16, the attachment parts 52, 62 and the attachment part 40 are shown in the fully assembled implanted configuration. The apical portion of the base section 42 of the attachment part 40 is attached to the ligament overlying the anterior part of the sacrum 20. The end section 54 of the attachment part 52 has been attached to the outer surface of the anterior vaginal wall 16 near the apex of the vagina 12, and the end section 64 of the attachment part 62 has been attached to the outer surface of the posterior vaginal wall 18 near the apex of the vagina 12.

Still referring to FIG. 16, the flap 43 of the attachment part 40 has been inserted through the first slot 58 of the attachment part 52, and the distal end of the flap 43 has been attached to the attachment part 40. Likewise, the flaps 44, 45, 46 have been attached to the attachment parts 52, 62. The loops formed by the flaps 43, 44, 45, 46 exert a force in direction A on the attachment parts 52, 62, which are attached to the vagina 12 as described above and shown in FIG. 16. This suspends the vagina 12 from the sacrum 20 thereby treating prolapse.

Other variations in the suspension devices are possible. An alternative to attachment part 22 can be a vaginal attachment part including a first end section having two flaps extending away from the first end section and including a second opposite end section having two flaps extending from the second end section. An alternative to the attachment part 40 can be a sacral attachment part having a first end section and a second opposite end section wherein the second opposite end section has four slots. Sutures in the ligament overlying the anterior part of the sacrum 20 can be attached to the apical portion of the base section of this sacral attachment part, and using a pulley stitch, the base section of this sacral attachment part can be affixed to the sacrum. The surgeon attaches the first end section of this alternative vaginal attachment part to the outer surface of the anterior vaginal wall 16 near the apex 13 of the vagina 12, and attaches the second end section 25 of this alternative vaginal attachment part 22 to the outer surface of the posterior vaginal wall 18 near the apex 13 of the vagina 12. The surgeon arranges each of the four tensioning flaps of this alternative vaginal attachment part in one of the slots of the alternative sacral attachment part, and the flaps are tensioned and attached as above.

In another variation in the suspension devices, each of the vaginal attachment part and the sacral attachment part includes some slots and some tensioning flaps. Thus, the tensioning flaps can be on either the part attached to the sacrum or the part attached to the vagina or on any combination therein.

In yet another variation in the suspension devices, the attachment parts 52, 62 can each be a vaginal attachment part including an end section having two flaps extending away from the end section. An alternative to the attachment part 40 can be a sacral attachment part having a first end section and a second opposite end section wherein the second opposite end section has four slots. Sutures in the ligament overlying the anterior part of the sacrum 20 can be attached to the apical portion of the base section of this sacral attachment part, and using a pulley stitch, the base section of this sacral attachment part can be affixed to the sacrum. The surgeon attaches one alternative vaginal attachment part to the outer surface of the anterior vaginal wall 16 near the apex 13 of the vagina 12, and attaches the other separate alternative vaginal attachment part 22 to the outer surface of the posterior vaginal wall 18 near the apex 13 of the vagina 12. The surgeon arranges each of the two tensioning flaps of one alternative vaginal attachment part and each of the two tensioning flaps of the other separate alternative vaginal attachment part in one of the slots of the alternative sacral attachment part, and the flaps are tensioned and attached as above.

In still another variation in the suspension devices, a two piece construction can be used where one part coming from the sacrum is also attached to the vagina and the other part that is attached to the vagina is connected to the other and tensioned.

While the invention has been described as including a method, an implantable suspension device, and a surgical instrument for treating vaginal vault prolapse, it should be understood that the invention can also adapted for use in the treatment of prolapse of other pelvic organs (e.g., uterus or bladder). Thus, although the present invention has been described in detail with reference to certain embodiments, one skilled in the art will appreciate that the present invention can be practiced by other than the described embodiments, which have been presented for purposes of illustration and not of limitation. Therefore, the scope of the invention should not be limited to the description of the embodiments contained herein.

INDUSTRIAL APPLICABILITY

The invention provides an implantable medical device and a surgical instrument for using the device in a procedure for the treatment of pelvic organ prolapse.

What is claimed is:

1. A method for treating pelvic organ prolapse in a patient, the method comprising:
 (a) forming an incision in a vaginal wall;
 (b) passing a first attachment part through the incision;
 (c) affixing the first attachment part to the sacrum or tissue adjacent the sacrum of the patient;
 (d) affixing a separate second attachment part to a wall of the pelvic organ; and
 (e) thereafter affixing the second attachment part to the first attachment part thereby suspending the pelvic organ from the sacrum or the tissue adjacent the sacrum,
 wherein step (c) comprises placing sutures in a ligament overlying an anterior part of the sacrum, and attaching the sutures to the first attachment part.

2. The method of claim 1 wherein:
 the pelvic organ is the vagina.

3. The method of claim 2 wherein:
 step (a) comprises forming the incision in an apex of the vagina.

4. The method of claim 3 wherein:
 step (c) comprises inserting a laparoscopic needle driver, or a direct suture device, or a suture capturing device through the apex of the vagina, and using the laparoscopic needle driver, the direct suture device, or the suture capturing device to place sutures in the ligament overlying the anterior part of the sacrum.

5. The method of claim 1 wherein:
 step (d) comprises affixing a first end section of the second attachment part to a first vaginal wall section near an apex of the vagina, and affixing a second end section of the second attachment part to an opposite second vaginal wall section near the apex of the vagina.

6. The method of claim 5 wherein:
 the first vaginal wall section is an anterior vaginal wall section, and
 the second vaginal wall section is a posterior vaginal wall section.

7. The method of claim 5 wherein:
the second attachment part includes an intermediate section between the first end section and the second end section, and
step (e) comprises affixing the intermediate section of the second attachment part to the first attachment part.

8. The method of claim 7 wherein:
step (e) comprises affixing the intermediate section of the second attachment part to the first attachment part by looping a flap of the first attachment part though an opening and a slot in the intermediate section of the second attachment part and attaching the flap to the first attachment part.

9. The method of claim 8 wherein:
step (e) comprises by looping three additional flaps of the first attachment part though the opening and three additional slots in the intermediate section of the second attachment part and attaching each additional flap to the first attachment part.

10. The method of claim 8 wherein:
step (e) comprises engaging the flap of the first attachment part with a hook of a surgical instrument, moving the instrument toward the sacrum to position the flap of the first attachment part adjacent a section of the first attachment part, and attaching the flap to the first attachment part.

11. The method of claim 10 wherein:
step (e) comprises measuring tension on the hook of the surgical instrument, and moving the instrument toward the sacrum until the tension reaches a predetermined tension.

12. The method of claim 11 wherein:
the tension is measured with a tension gauge coupled to the hook.

13. The method of claim 7 wherein:
step (e) comprises affixing the intermediate section of the second attachment part to the first attachment part by looping a first flap of the first attachment part though an opening and a first slot in the intermediate section of the second attachment part and attaching the first flap to the first attachment part, and
step (e) further comprises affixing the intermediate section of the second attachment part to the first attachment part by looping a second flap of the first attachment part though the opening and a second slot in the intermediate section of the second attachment part and attaching the second flap to the first attachment part.

14. The method of claim 13 wherein:
the first slot and the second slot are on opposite sides of the opening.

15. The method of claim 7 wherein:
step (e) comprises visualizing the first attachment part through an opening in the second attachment part, and affixing the intermediate section of the second attachment part to the first attachment part by looping a flap of the first attachment part though the opening and a slot in the intermediate section of the second attachment part and attaching the flap to the first attachment part.

16. The method of claim 1 wherein:
step (e) comprises affixing the second attachment part to the first attachment part by looping a flap of the second attachment part though a slot in the first attachment part and attaching the flap to the second attachment part.

17. A method for treating pelvic organ prolapse in a patient, the method comprising:
(a) forming an incision in a vaginal wall;
(b) passing a first attachment part through the incision;
(c) affixing the first attachment part to the sacrum or tissue adjacent the sacrum of the patient;
(d) affixing a separate second attachment part to a first wall section of a pelvic organ;
(e) affixing a separate third attachment part to a second wall section of the pelvic organ; and
(e) thereafter affixing the second attachment part and the third attachment part to the first attachment part thereby suspending the pelvic organ from the sacrum or the tissue adjacent the sacrum,
wherein step (c) comprises placing sutures in a ligament overlying an anterior part of the sacrum, and attaching the sutures to the first attachment part.

18. The method of claim 17 wherein:
the pelvic organ is the vagina.

19. The method of claim 18 wherein:
the first wall section is an anterior vaginal wall section adjacent an apex of the vagina, and
the second wall section is a posterior vaginal wall section adjacent the apex of the vagina.

* * * * *